Figure 1:
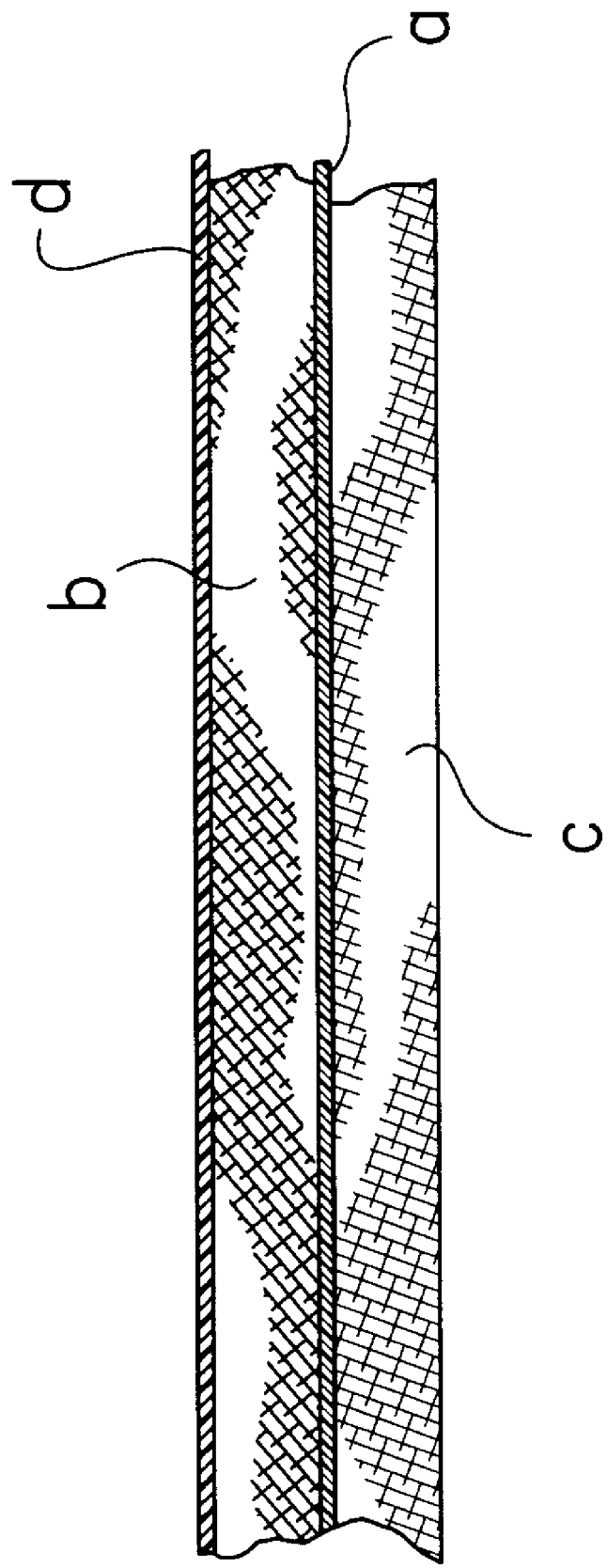

United States Patent [19]
Gilding

[11] Patent Number: 5,998,692
[45] Date of Patent: Dec. 7, 1999

[54] WOUND DRESSING

[75] Inventor: Denis Keith Gilding, Cheshire, United Kingdom

[73] Assignee: Innovative Technologies Limited, Winsford, United Kingdom

[21] Appl. No.: 08/875,459

[22] PCT Filed: Jan. 26, 1996

[86] PCT No.: PCT/GB96/00174

§ 371 Date: Oct. 6, 1997

§ 102(e) Date: Oct. 6, 1997

[87] PCT Pub. No.: WO96/22753

PCT Pub. Date: Aug. 1, 1996

[30] Foreign Application Priority Data

Jan. 26, 1995 [GB] United Kingdom .................. 9501513
Jan. 26, 1995 [GB] United Kingdom .................. 9501515

[51] Int. Cl.$^6$ ............................................. A61F 13/00

[52] U.S. Cl. ............................................. 602/41; 602/53

[58] Field of Search .................. 602/41–59; 128/888, 128/889; 428/368

[56] References Cited

U.S. PATENT DOCUMENTS

| | | | |
|---|---|---|---|
| 4,743,499 | 5/1988 | Volke | 602/42 |
| 5,470,576 | 11/1995 | Patel | 424/445 |
| 5,482,932 | 1/1996 | Thompson | 514/56 |
| 5,571,079 | 11/1996 | Bello et al. | 602/46 |

*Primary Examiner*—Richard J. Apley
*Assistant Examiner*—Kim M. Lee
*Attorney, Agent, or Firm*—Woodard, Emhardt, Naughton Moriarty & McNett

[57] ABSTRACT

A wound dressing beneficial for use on high exuding wounds comprising a breathable film having an increased MTRV capability and an absorbent layer having high fluid holding capacity located on the film side remote from the wound. The dressing is further characterized by a low profile suitable for use under garments. The dressing may further comprise a third layer located on the film side proximal to the wound that is alternatively either absorbent to further control moisture levels at the wound site, or alternatively promotes the production of exudate to facilitate the flushing of the wound. The dressing may also comprise a compressive element on the side of the absorbent layer remote from the wound to provide compressive therapy capability.

16 Claims, 1 Drawing Sheet

WOUND DRESSING

The present invention relates to wound dressings.

FIG. 1 is a diagrammatic rendering of a transverse segment through one embodiment of the present inventive wound dressing showing the relative positioning of breathable film (a), absorbent fabric material (b), wound contact layer (c), and compression element (d).

According to a fist aspect of the present invention there is provided, for use as a wound dressing, the combination of
(a) a breathable film which is of increased MVTR capability in the presence of a liquid water as come to moisture vapor alone, and
(b) an absorbent fabric material for location on the side of the film remote from the wound to absorb exudate which has passed through the film.

The film is one which is of increased breathability in the presence of liquid water as compared to moisture vapor alone. MVTR in the presence of liquid water may be measured by ASTM E96BW whereas MVTR in the presence of moisture vapor alone may be measured by ASTM E96B Water Method). Preferably the value of the breathability in the presence of liquid water is at least twice and preferably at least three times that in the presence of moisture vapor alone. Typically the film will be of a material which has an MVTR in the presence of moisture vapor alone (ASTM E96B) of 2,000 to 2,500 g m$^{+2}$ 24 hr$^{-1}$ and an MVTR in the presence of liquid water (ASTM E96BW) in the range 6,000 to 30,000 g m$^{+2}$ 24 hr$^{-1}$ (e.g. 6,000 to 10,000 g m$^{-2}$ 24 hr$^{+1}$).

Typically the film will have a thickness of 30–70 microns, more preferably 40–60 microns, e.g. about 50 microns.

The film may for example be of polyurethane. Suitable films are available from Innovative Technologies Limited under the designations IT325, IT425 and IT625.

The absorbent fabric material is preferably a highly absorbent gauze or gauze-like material (e.g. a highly absorbent cotton gauze). One example of a suitable gauze material is one comprised of calcium and sodium alginate fibers as available from Innovative Technologies Limited.

The breathable film (i.e (a)) of the above combination may be used as a wound contact layer and looted in position by the patient without the need for expert medical help. The film also acts as a microbial barrier over the wound. The absorbent material is then applied to the side of the film remote from the wound and may be retained in position by tape, film or the like.

The advantage of the combination is that fluid is drawn tough the film and contained in the absorbing layer thereby preventing maceration. The absorbent fabric material is thin with a high fluid holding capacity and provides a low profile wound dressing system suitable for use with normal footwear when used on high exuding ulcers (e.g. on a patient's ankle).

In a first preferred embodiment of the invention the combination of (a) and (b) may further comprise
(c)(i) a further absorbent layer (as a wound contact layer) for use in cases where fluid production by the wound may be too rapid for the breathable film to be used alone as the primary dressing.

The layer (c)(i) may be used as the primary wound contact layer to absorb medium to high exudate levels from wounds such as venous stasis ulcers. The fluid from the wound then passes through layer (a) for absorption by layer (b). Examples of layer (c)(i) include alginates and other dressings. Particular examples of alginates which may be used are as disclosed in our PCT Patent Application No. GB95/02284.

The alginate may be in the form of a silver alginate (the silver providing anti-microbial properties) or a zinc alginate (zinc providing a stimulus in the later stage of the healing process).

Further examples for layer c(i) include the materials disclosed in our PCT Application No. GB95/02542. Specific examples include pectinised amorphous gels.

By suitable choice of the breathable film, it is possible to control the level of hydration of the alginate primary dressing and thus manipulate healing capability.

Alternatively the combination of (a) and (b) may further comprise (c)(ii) as the primary wound contact layer, a layer promoting production of exudate that will flush infection from wound tissues as a preliminary to healing the wound. Bacteria from the wound may be contained within layer (c)(ii) and the fluid transmitted through the film (a) into layer (b).

Layer c(ii) may for example comprise copper alginate or copper borate impregnated gauze.

In all of the above cases, layer (b) may be fixed in place by a conventional tape (so that excess moisture vapor is vented to atmosphere) or contained by a second film which is either occlusive or semi-occlusive. With an occlusive film, the fluid handling capability of the wound is controlled by the absorption capacity of layer (b).

A further (second) embodiment of the invention relates to a wound dressing for use in compression therapy, particularly (but not exclusively) for use in the treatment of venous stasis ulcers.

It is now becoming universally accepted that compression therapy is mandatory for healing many advanced venous stasis ulcers where venous valves have become incompetent. The compression is used to restore calf pump action in the legs.

Conventional compression therapy involves use of a four layer dressing which comprises
(1) a gauze like primary dressing
(2) a thick plaster-cast type cotton wadding
(3) a crepe bandage to locate the wadding in position and act as in initial compression element, and
(4) a rubberised compression bandage.

The dressing is generally wound front the foot to the knee of a patient. When the patient walks, the compression bandage serves to provide the abovementioned compression to restore pump action in the legs.

The dressing does however have the disadvantage that, whilst being potentially effective, its bulk does not allow the patient to wear his/her normal shoes. As a result patients tend not to walk (as is required to restore venous return to close to normal levels) but rather tend to become sedentary because of the bulk of the dressing.

There are also the addition disadvantages of discomfort due to heat and skin irritation caused by these bulky dressings.

To meet the problem, the second preferred embodiment of the invention provides for use as a wound dressing, the combination of (a) and (b) as defined above, and
(d) a compression element.

The combination of (a), (b) and (d) may for example be provided as individual components in a single package.

The dressing is applied to the wound such that, going from the wound to the outside of the dressing, the layers are in the order (a), (b), (d). Such dressings are considerably less bulky than the conventional compression bandage systems due to the low volume of the layer of an absorbent fabric material and obviate the disadvantages described above in relation to conventional compression therapy. For treatment of venous stasis ulcers, the dressing may be wound from the foot to the knee of the patient. Patients receiving such treatment are able to wear normal footwear and can therefore remain mobile and active.

The compression element (d) may be any suitable elastic or resilient element. Examples include a traditional crepe bandage, a thin microporous membrane without adhesive and a traditional rubberised occlusive bandage.

For preference, the compression element is a microporous membrane most suitably having a thickness of 0.4 to 0.8 mm and an MVTR in the range 6,000 to 10,000 g m$^{+2}$ 24 hr$^{-1}$, e.g. about 8,000 g m$^{-2}$ 24 hr$^{-1}$. A suitable membrane is available under the name Flexipore.

In this (second) embodiment of the invention the breathable film (i.e (a)) may be used as a wound contact layer and (as described above) located in position by the patient without the need for expert medical help. The absorbent material is then applied to the side of the film remote from the wound and may be retained in position by the compression element.

The advantage of the combination is that fluid is drawn through the film and contained in the absorbing layer thereby preventing maceration. If the compression element is a microporous membrane then this will serve to vent moisture to atmosphere.

By suitable choice of the breathable film, it is possible to control the level of hydration of the wound and therefore manipulate healing capability.

The combination of (a), (b) and (d) may further comprise layers c(i) or c(ii) as described more fully above as wound contact layers.

FIG. 1 illustrates one embodiment of the present inventive wound dressing to foster a better understanding of one arrangement of the elements of the dressing. It is to be understood that the diagram is by way of example only and that no limitation of the scope of the invention is intended thereby. The embodiment shown in FIG. 1 shows a breathable film (a) having opposing first and second sides, absorbent fabric material (b) having a first and a second side with said second side being disposed against the first side of breathable film (a), wound contact layer (c) disposed against the second side of breathable film (a), and a compression element (d) disposed against the first side of absorbent fabric material (b). Other embodiments are also described in the specification and any alterations and further modifications of the embodiments shown or described, and further applications of the principles of the invention as described herein, are contemplated as would normally occur to one skilled in the art to which the invention relates. Such modifications to and equivalents of the elements of the disclosed invention that come within the spirit of the invention as defined by the following claims are contemplated and their protection is desired.

I claim:

1. A wound dressing comprising:
   (a) a breathable film which is of increased MVTR capability in the presence of a liquid water as compared to moisture vapor alone, said film having opposing first and second sides;
   (b) an absorbent fabric material having first and second sides, the second side of the absorbent fabric material being disposed against the first side of the film to absorb exudate which has passed through the film;
   (c) a further absorbent layer as a wound contact layer disposed against the second side of the film; and
   (d) a compression element disposed against the first side of the absorbent fabric material.

2. The dressing of claim 1 wherein layer (c) is an alginate.

3. The dressing of claim 2 wherein the alginate is a silver alginate or a zinc alginate.

4. The dressing of claim 1 wherein layer (c) is a pectinised amorphous gel.

5. A wound dressing comprising:
   (a) a breathable film which is of increased MVTR capability in the presence of a liquid water as compared to moisture vapor alone, said film having opposing first and second sides;
   (b) an absorbent fabric material having first and second sides, the second side of the absorbent fabric material being disposed against the first side of the film to absorb exudate which has passed through the film;
   (c) a wound contact layer disposed against the second side of the film, said wound contact layer being able to promote production of exudate that will flush infection from wound tissues as a preliminary to healing the wound; and
   (d) a compression element disposed against the first side of said absorbent fabric material.

6. The dressing of claim 5 wherein layer (c) comprises copper alginate or copper borate impregnated gauze.

7. The dressing of either claim 1 or 5 wherein said breathable film has a breathability in the presence of liquid water at least twice that in the presence of moisture vapor alone.

8. The dressing of either claim 1 or 5 wherein the breathable film has a breathability in the presence of liquid water at least three times that in the presence of moisture vapor alone.

9. The dressing of either claim 1 or 5 wherein the breathable film has an MVTR in the presence of moisture vapor alone of 2,000 to 2,500 g m$^{-2}$ 24 hr$^{-1}$ and an MVTR in the presence of liquid water in the range of 6,000 to 30,000 g m$^{-2}$ 24 hr$^{-1}$.

10. The dressing of either claim 1 or 5 wherein the film has a thickness of 30–70 microns.

11. The dressing of either claim 1 or 5 wherein the film has a thickness of 40–60 microns.

12. The dressing of either claim 1 or 5 wherein the film is of a polyurethane.

13. The dressing of either claim 1 or 5 wherein the compression element is a crepe bandage or a rubberized occlusive bandage.

14. The dressing of either claim 1 or 5 wherein the compression element is a microporous membrane.

15. The dressing of claim 14 wherein the microporous membrane has a thickness of 0.4 to 0.8 mm.

16. The dressing of claim 14 wherein the microporous membrane has an MVTR in the range of 6,000 to 10,000 g m$^{-2}$ 24 hr$^{-1}$.

* * * * *